US011624794B2

(12) United States Patent
Harris et al.

(10) Patent No.: US 11,624,794 B2
(45) Date of Patent: Apr. 11, 2023

(54) AUTOMATIC PROTOCOLLING TO REDUCE SYSTEM AND PATIENT INTERACTIONS

(71) Applicant: SYNAPTIVE MEDICAL INC., Toronto (CA)

(72) Inventors: Chad Tyler Harris, Toronto (CA); Jeff Alan Stainsby, Toronto (CA); Andrew Thomas Curtis, Ajax (CA); Philip J. Beatty, Thornhill (CA); Curtis Nathan Wiens, Toronto (CA)

(73) Assignee: Synaptive Medical Inc.

( * ) Notice: Subject to any disclaimer, the term of this patent is extended or adjusted under 35 U.S.C. 154(b) by 0 days.

(21) Appl. No.: 17/445,249

(22) Filed: Aug. 17, 2021

(65) Prior Publication Data
US 2022/0050160 A1 Feb. 17, 2022

Related U.S. Application Data

(60) Provisional application No. 63/066,357, filed on Aug. 17, 2020.

(51) Int. Cl.
G01R 33/54 (2006.01)
A61B 5/055 (2006.01)
G01R 33/28 (2006.01)

(52) U.S. Cl.
CPC ............ *G01R 33/543* (2013.01); *A61B 5/055* (2013.01); *G01R 33/288* (2013.01)

(58) Field of Classification Search
CPC .. G01R 33/543; G01R 33/288; G01R 33/546; A61B 5/055
See application file for complete search history.

(56) References Cited

U.S. PATENT DOCUMENTS

| 2004/0017195 | A1* | 1/2004 | Kassai | G01R 33/3856 324/315 |
| 2011/0148412 | A1 | 6/2011 | Kanazawa | |
| 2013/0023753 | A1* | 1/2013 | Kawamura | A61B 5/055 600/410 |
| 2019/0320934 | A1* | 10/2019 | Odry | G16H 10/60 |

OTHER PUBLICATIONS

Ravi et al., "Intelligent Protocolling for Autonomous MRI", Proc. Intl. Soc. Mag. Reson. Med. 28 (2020), 4154.
(Continued)

*Primary Examiner* — G. M. A Hyder

(57) ABSTRACT

An automatic protocolling system and methods involving a processor operable by way of a set of executable instructions storable in relation to a nontransient memory device, the set of executable instructions configuring the processor to: receive information relating to an initial protocol comprising an initial ordering of a plurality of sequences, the information comprising data relating to an interaction extent value of at least one of an imaging system and a patient as a function of time corresponding to each sequence in the plurality of sequences, the data relating to a time-integrated effect of each sequence in the plurality of sequences; and dynamically determine an alternative protocol comprising an alternative ordering of the plurality of sequences based on the time-integrated effect, whereby an alternative protocol is provided.

19 Claims, 6 Drawing Sheets

(56) References Cited

OTHER PUBLICATIONS

Search report issued by the Intellectual Property Office of the UK in relation to GB Application No. GB2111797.3 dated Apr. 4, 2022.
Magnetic Resonance in Medicine, vol. 81, 2018, Carluccio Giuseppe et al, "Optimization of the order and spacing of sequences in an MRI exam to reduce the maximum temperature and thermal dose", pp. 2161-2166.

* cited by examiner

AUTOMATIC PROTOCOLLING TO REDUCE SYSTEM AND PATIENT INTERACTIONS

CROSS-REFERENCE TO RELATED APPLICATION(S)

This document is a nonprovisional patent application claiming the benefit of, and priority to, U.S. Patent Application Ser. No. 63/066,357, entitled "AUTOMATIC PROTOCOLLING TO REDUCE SYSTEM AND PATIENT INTERACTIONS," and filed on Aug. 17, 2020, which is hereby incorporated by reference herein its entirety.

FIELD

The subject matter of the present disclosure generally relates to systems and methods for magnetic resonance imaging ("MRI").

BACKGROUND

In the related art, some sequences have larger effects on the system than others. For instance, steady-state free precession magnetic resonance imaging (SSFP MRI) and echo-planar magnetic resonance imaging (EPI MRI) are technologies which use large-gradient waveforms. Such large-gradient waveforms tend to strain a gradient cooling system. Further such large-gradient waveforms tend to substantially interact with a magnet of a magnetic resonance system. Similarly, fast spin-echo imaging typically uses larger B1+ magnetic fields which can result in substantial transmit-coil heating. If multiple sequences with similar magnetic resonance system interactions are run repeatedly, the hardware limits (needed to protect the system from breaking) are triggered, thereby causing a scanner failure or delay in scanning. In a worst-case scenario, a quench or hardware damage is induced.

In a similar, yet different related art scenario, some sequences interact more with a patient than other sequences. For example, if the patient has an implanted device, either a particular imaging sequence deposits more energy, due to large B1+ magnetic field, or gradient-coil-induced eddy current forms in the implant, thereby causing heating. In addition to interactions with implanted devices, acoustic energy is much higher for some sequences than others. In the related art, automatic modifications to imaging protocols have been made by changing pulse sequence parameters, e.g., repetition time (TR), resolution, number of averages, etc., which can result in a reduction of overall scan time while minimizing the penalty in signal-to-noise ratio (SNR). Other related art efforts involve an automatic alignment of imaging sequences to certain anatomical structures. Therefore, a long-felt need exists for an overall improvement of a patient's MRI imaging experience.

SUMMARY

In addressing at least many of the challenges experienced in the related art, an automatic protocolling system and methods involve automatically ordering an MRI imaging protocol for at least one of reducing intra-scanner hardware interactions, reducing scanner-to-patient interactions, and improving overall patient experience, in accordance with embodiments of the present disclosure. The automatic protocolling system and methods involve strategically, intelligently, ordering certain imaging sequences, e.g., some calibration scans or some 3D anatomical sequences, that are relatively benign in relation to a scanner or a patient interaction, in relation to other imaging sequences. By intelligently selecting, or determining, an order of a plurality of imaging sequences within a medical examination, e.g., involving MRI imaging, such as by spacing apart at least one greater-interacting sequence and, therebetween, interleaving at least one less-interacting sequence, the automatic protocolling system and methods involve artificially, intelligently, selecting, or determining, and automatically executing a protocol, such as an entire medical imaging protocol, in at least one of a more time-efficient manner and a safer manner than related art protocolling systems and methods, for at least one of imaging system hardware and a patient, in accordance with embodiments of the present disclosure. Optionally, ordering comprises using artificial intelligence.

Further, a patient's memory of an imaging experience has been found to be influenced to a greater extent by events occurring at the end of an MRI imaging experience, rather than at the beginning of the MRI imaging experience. For example, the automatic protocolling system and methods involve intelligently selecting, or determining, an order of a plurality of imaging sequences within a medical examination by spacing apart at least one sequence that is deemed "louder" relative to at least one sequence that is deemed "quieter," whereby an overall noise energy, over a set duration of time, is reduced, whereby negative effects, such as hearing loss, are reduced.

In some embodiments of the present disclosure, the automatic protocolling system and methods further involve intelligently selecting, or determining, for at least one sequence on the plurality of sequences, at least one pulse sequence parameter, e.g., comprising at least one of a repetition time TR, a resolution, a number of averages, etc., in order to reduce an overall imaging scan time while minimizing a SNR penalty. Embodiments of the present disclosure involve the use of information relating to specific system interactions, e.g., information relating to gradient-coil heating, transmit-coil heating, magnet heating, etc. Embodiments of the present disclosure further involve automatically ordering sequences within a medical examination, such as by automatically replacing scanner deadtime with functional or useful, non-interacting, sequences. Accordingly, embodiments of the present disclosure generally involve intelligently selecting, determining, or ordering a set of magnetic resonance (MR) sequences in order to reduce overall interactions with the MRI system and/or the patient.

In an embodiment of the present disclosure, an automatic protocolling system comprises a processor operable by way of a set of executable instructions storable in relation to a nontransient memory device, the set of executable instructions configuring the processor to: receive information relating to an initial protocol comprising an initial ordering of a plurality of sequences, the information comprising data relating to an interaction extent value of at least one of an imaging system and a patient as a function of time corresponding to each sequence in the plurality of sequences; and dynamically determine an alternative protocol comprising an alternative ordering of the plurality of sequences, whereby an alternative protocol is provided.

In an embodiment of the present disclosure, a method of providing an automatic protocolling system comprises providing a processor operable by way of a set of executable instructions storable in relation to a nontransient memory device, the set of executable instructions configuring the processor to: receive information relating to an initial protocol comprising an initial ordering of a plurality of sequences, the information comprising data relating to an interaction extent value of at least one of an imaging system and a patient as a function of time corresponding to each sequence in the plurality of sequences; and dynamically determine an alternative protocol comprising an alternative ordering of the plurality of sequences, whereby an alternative protocol is provided.

In an embodiment of the present disclosure, a method of automatically protocolling by way of an automatic protocolling system comprises: providing the automatic protocolling system, providing the automatic protocolling system comprising providing a processor operable by way of a set of executable instructions storable in relation to a nontransient memory device, the set of executable instructions configuring the processor to: receive information relating to an initial protocol comprising an initial ordering of a plurality of sequences, the information comprising data relating to an interaction extent value of at least one of an imaging system and a patient as a function of time corresponding to each sequence in the plurality of sequences; and dynamically determine an alternative protocol comprising an alternative ordering of the plurality of sequences, whereby an alternative protocol is provided; by using the automatic protocolling system, receiving the information relating to the initial protocol comprising the initial ordering of the plurality of sequences; and dynamically determining the alternative protocol comprising the alternative ordering of the plurality of sequences, thereby providing the alternative protocol; and dynamically instructing an imaging system to operate by using the alternative protocol.

Some of the features in the present disclosure are broadly described in order that the section, entitled Detailed Description, is better understood and that the contribution to the art by the present disclosure is better appreciated. Additional features of the present disclosure are described hereinafter. In this respect, the present disclosure is not limited in its implementation to the details of the components or steps as set forth herein or as illustrated in the several figures of the Drawing, but are capable of being carried out in various ways which are also encompassed by the present disclosure. Also, the phraseology and terminology employed herein are used for illustrative purposes in the description and are not regarded as limiting.

BRIEF DESCRIPTION OF THE DRAWING(S)

The above, and other, aspects, and features, of the several embodiments in the present disclosure will be more apparent from the following Detailed Description as presented in conjunction with the following several figures of the Drawing. The several embodiments of the present disclosure are shown by examples only as follows.

Figure 1A:
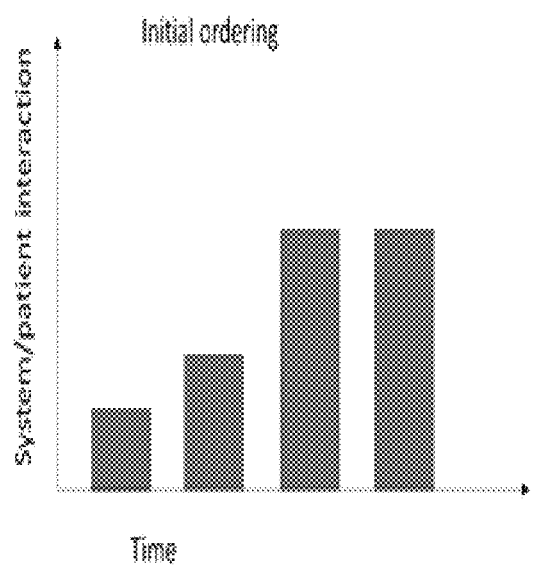
FIG. 1A is a graph illustrating an interaction extent of at least one of an imaging system and a patient as a function of time, based on an initial ordering of a plurality of sequences.

Corresponding reference numerals or characters indicate corresponding components throughout the several figures of the Drawing. Elements in the several figures are illustrated for simplicity and clarity and have not necessarily been drawn to scale. For example, the dimensions of some elements in the figures are emphasized relative to other elements for facilitating understanding of the various presently disclosed embodiments. Also, well-understood elements that are useful, or necessary, in commercially feasible embodiment are often not depicted to facilitate a less obstructed view of these various embodiments of the present disclosure.

DETAILED DESCRIPTION

The systems and methods described herein are useful in the field of imaging and tracking, such as used in relation to neurosurgery, including oncological care, neurodegenerative disease, stroke, brain trauma, and orthopedic surgery. The subject matter of the present disclosure is applicable to imaging and tracking in relation to other conditions or fields of medicine. While the present disclosure describes examples in the context of imaging and/or tracking in relation to neurosurgery, the subject matter of the present disclosure is applicable to other surgical procedures that use imaging, such as MRI.

Various example apparatuses or processes are herein described. No herein described example embodiment limits any claimed embodiment; and any claimed embodiments may cover processes or apparatuses that differ from those examples herein described. The claimed embodiments are not limited to apparatuses or processes having all the features of any one apparatus or process herein described or to features common to multiple or all the apparatuses or processes herein described. The claimed embodiments optionally comprise any combination or permutation of any of the herein described elements, limitations, and/or features.

Furthermore, numerous specific details are set forth in order to provide a thorough understanding of the present disclosure. The embodiments herein described can be practiced without these specific details. In other instances, well-known methods, procedures, and components have not been described in detail so as not to obscure the herein described embodiments.

As used herein, the terms, "comprises" and "comprising" are to be construed as being inclusive and open ended, and not exclusive. Specifically, when used in the specification and claims, the terms, "comprises" and "comprising" and variations thereof denote the specified features, steps, or components that are included; however, these terms are not to be interpreted to exclude the presence of other features, steps, or components.

As used herein, the term "exemplary" or "example" denotes "serving as an example, instance, or illustration," and should not be construed as preferred or advantageous over other configurations herein disclosed.

As used herein, the terms "about," "approximately," and "substantially" cover variations that may exist in an upper limit and a lower limit of any range of value(s), such as variations in properties, parameters, and dimensions. In one non-limiting example, the terms "about," "approximately," and "substantially" are denote plus or minus 10 percent or less.

Unless defined otherwise, all technical terms and scientific terms used herein are intended to have the same definition as understood by one of ordinary skill in the art.

Referring to FIG. 1A, this graph illustrates an interaction extent of at least one of an imaging system and a patient (ordinate axis) as a function of time (abscissa axis), based on an initial ordering 100A of a plurality of sequences, in accordance with an embodiment of the present disclosure. Each sequence of the plurality of sequences having a corresponding interaction extent value of at least one of an imaging system and a patient (ordinate axis) as a function of time (abscissa axis).

Figure 1B:
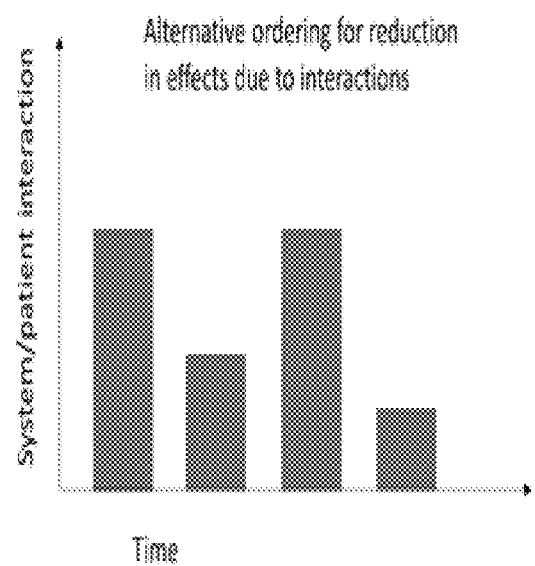
FIG. 1B is a graph illustrating an interaction extent of at least one of an imaging system and a patient as a function of time, as shown in FIG. 1A, based on an alternative ordering of the plurality of sequences, wherein the alternative ordering is automatically determined by way of an automatic protocolling system.

Referring to FIG. 1B, this graph illustrates an interaction extent of at least one of an imaging system and a patient (ordinate axis) as a function of time (abscissa axis), as shown in FIG. 1A, based on an alternative ordering 100B of the plurality of sequences, wherein the alternative ordering 100B is automatically determined by way of an automatic protocolling system S (FIG. 4), in accordance with an embodiment of the present disclosure. The alternative ordering 100B facilitates an overall reduction in interaction effects. The interaction effects comprise a peak temperature of at least one of a magnet, a transmit-coil, a gradient-coil, and a patient over a plurality of sequences. The alternative ordering 100B is based on at least one of an individual interaction effect of each sequence in the plurality of sequences and a time-integrated effect of each sequence in the plurality of sequences.

Referring back to FIGS. 1A and 1B, the interaction extent of an imaging system is evaluated by at least one of measuring and determining a value, such as a value corresponding to a root-mean-square (RMS) of a magnetic field B1+ over a sequence duration, wherein B1 comprises a magnetic field value associated with an RF transmit system of the imaging system, and a value, corresponding to an RMS of a change in a magnetic field as a function of temperature, dB/dt, over a sequence duration, wherein B comprises a magnetic field value, and wherein t comprises a time value, e.g., in the case of at least one of a gradient coil heating, a gradient-induced implant heating, a gradient-induced system heating, and an overall imaging system heating). Further, the interaction extent of an imaging system is evaluated by at least one of measuring and determining a value, corresponding to a sequence, based on a convolution of an impulse response with a plurality of sequence waveforms, by generating a heating-impulse response for a transmit-coil, a gradient system, and a magnet for a given set of input waveforms. Furthermore, the interaction extent of an imaging system is evaluated by at least one of measuring and determining a value, corresponding to an equivalent sound pressure level that is created by the sequence over a set period of time.

Still referring back to FIGS. 1A and 1B, in other embodiments, the interaction extent of an imaging system is evaluated by at least one of measuring and determining a value, such as a value corresponding to a magnet temperature dependence relationship, the magnet temperature dependence relationship comprising at least one frequency component of at least one requested gradient waveform. Magnet heating may depend on a frequency component as well as on a raw RMS of a magnetic field as a function of temperature, dB/dt. In other embodiments, the interaction extent of an imaging system is evaluated by at least one of measuring and determining a value, corresponding to at least one of a magnet temperature increase, a transmit-coil temperature increase, a gradient-coil temperature increase in relation to a saved sequence protocol.

Still referring back to FIGS. 1A and 1B, the interaction extent of a patient is evaluated by at least one of measuring and determining a value, corresponding to at least one of a specific absorption rate (SAR) and a transmit-coil heating). Further, the interaction extent of a patient is evaluated by at least one of measuring and determining a value, corresponding to at least one overall patient experience metric for each sequence, wherein determining, e.g., strategically, intelligently ordering, certain imaging sequences, is based on an average patient experience rating over a set time interval, and wherein the average patient experience rating is determined by implementing a series of experiments. Furthermore, the interaction extent of a patient is evaluated by at least one of measuring and determining a value, corresponding to a plurality of overall patient experience metrics for each sequence.

Still referring back to FIGS. 1A and 1B, the system and methods of the present disclosure involve determining an optimal sequence organization comprising: evaluating each, and every, combination and each, and every, permutation of each, and every, parameter relating to each imaging sequence of a plurality of imaging sequences; selecting a plurality of imaging sequences based on a lowest total interaction extent, based on a lowest interaction extent of the imaging system and a lowest interaction extent of the patient; and ordering the plurality of imaging sequences, based on the lowest interaction extent of the imaging system and the lowest interaction extent of the patient, wherein each, and every, parameter, relating to each imaging sequence comprises at least one of an overall imaging system heating, a shortest scanner duration, including any downtime to reduce heating, a maximum acoustic energy over a set time interval, e.g., approximately 5 minutes), and the like.

Still referring back to FIGS. 1A and 1B, the system and methods of the present disclosure involve determining an optimal sequence organization comprising: ordering a plurality imaging sequences from a lowest total interaction extent to a highest total interaction extent, based on a lowest interaction extent of the imaging system and a lowest interaction extent of the patient to a highest interaction extent of the imaging system and a highest interaction extent of the patient; and ordering the plurality of imaging sequences, based on the lowest interaction extent of the imaging system and the lowest interaction extent of the patient, based on the lowest total interaction extent to the highest total interaction extent, whereby imaging information is maximized in the event of any interruption to operation of the imaging system, e.g., from overheating.

Still referring back to FIGS. 1A and 1B, the system and methods of the present disclosure alternatively involve determining an optimal sequence organization comprising: evaluating each, and every, combination and each, and every, permutation of each, and every, parameter relating to each imaging sequence of a plurality of imaging sequences; selecting a first imaging sequence of a plurality of imaging sequences based on a highest total interaction extent comprising a highest interaction extent of the imaging system and a highest interaction extent of the patient; selecting a second imaging sequence of the plurality of imaging sequences based on a lowest total interaction extent comprising a lowest interaction extent of the imaging system and a lowest interaction extent of the patient; selecting a third imaging sequence of the plurality of imaging sequences based on a second highest total interaction extent comprising a second highest interaction extent of the imaging system and a second highest interaction extent of the patient; selecting a fourth imaging sequence of the plurality of imaging sequences based on a second lowest total interaction extent comprising a second lowest interaction extent of the imaging system and a lowest highest interaction extent of the patient; and ordering the plurality of imaging sequences accordingly, wherein each, and every, parameter, relating to each imaging sequence comprises at least one of an overall imaging system heating, a shortest scanner duration, including any downtime to reduce heating, a maximum acoustic energy over a set time interval, e.g., approximately 5 minutes), and the like.

Figure 2A:
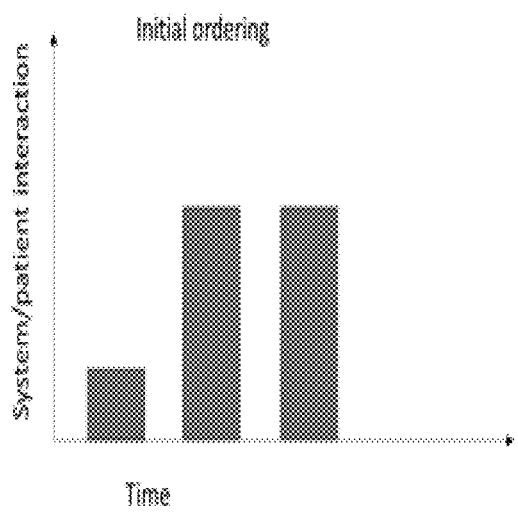
FIG. 2A is a graph illustrating another interaction extent of at least one of an imaging system and a patient as a function of time, based on another initial ordering of a plurality of sequences.

Referring to FIG. 2A, this graph illustrates another interaction extent of at least one of an imaging system and a patient (ordinate axis) as a function of time (abscissa axis), based on another initial ordering 200A of a plurality of sequences, in accordance with an embodiment of the present disclosure. Each sequence of the plurality of sequences having a corresponding interaction extent value of at least one of an imaging system and a patient (ordinate axis) as a function of time (abscissa axis).

Figure 2B:
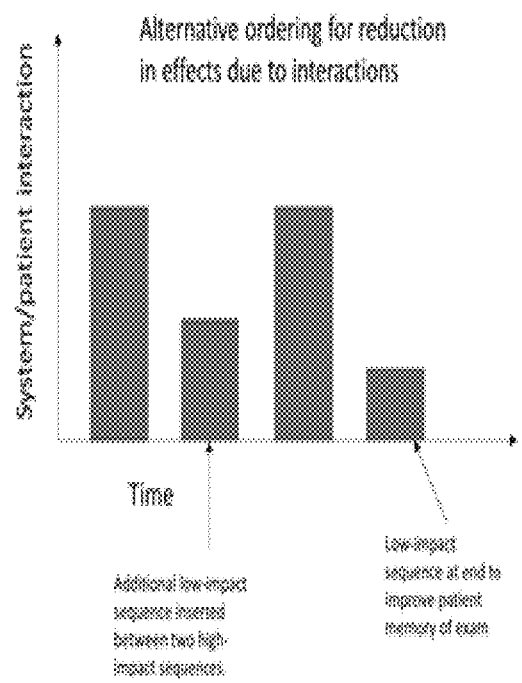
FIG. 2B is a graph illustrating another interaction extent of at least one of an imaging system and a patient as a function of time, as shown in FIG. 2A, based on an alternative ordering of the plurality of sequences, wherein the alternative ordering is automatically determined by way of an automatic protocolling system.

Referring to FIG. 2B, this graph illustrates another interaction extent of at least one of an imaging system and a patient (ordinate axis) as a function of time (abscissa axis), as shown in FIG. 2A, based on an alternative ordering 200B of the plurality of sequences, wherein the alternative ordering 200B is automatically determined by way of an automatic protocolling system S (FIG. 4), in accordance with an embodiment of the present disclosure. The alternative ordering 200B facilitates an overall reduction in interaction effects. The interaction effects comprise a peak temperature of at least one of a magnet, a transmit-coil, a gradient-coil, and a patient over a plurality of sequences. The alternative ordering 100B is based on at least one of an individual interaction effect of each sequence in the plurality of sequences and a time-integrated effect of each sequence in the plurality sequences.

Still referring to FIG. 2B, in situations where a gap between two highly-interacting sequences are to be run, the automatic protocolling system S will suggest, to a user, a set of non-interacting sequences to be run between the two highly-interacting sequences, rather than performing no action at all as would otherwise be the situation in the related art. In one implementation, the automatic protocolling system S automatically determines and instructs placement of non-interacting or low-interacting (low-impact) sequences between highly interacting sequences in order to at least one of: update calibration data, acquire partial or full quantitative data, or other data that may be useful for final diagnosis or image processing, by examples only.

Referring back to FIGS. 2A and 2B, the interaction extent of an imaging system is evaluated by at least one of measuring and determining a value, such as a value corresponding to a root-mean-square (RMS) of a magnetic field B1+ over a sequence duration, wherein B1 comprises a magnetic field value associated with an RF transmit system of the imaging system, and a value, corresponding to an RMS of a change in a magnetic field as a function of temperature, dB/dt, over a sequence duration, wherein B comprises a magnetic field value, and wherein t comprises a time value, e.g., in the case of at least one of a gradient coil heating, a gradient-induced implant heating, and a gradient-induced system heating). Further, the interaction extent of an imaging system is evaluated by at least one of measuring and determining a value, corresponding to a sequence, based on a convolution of an impulse response with a plurality of sequence waveforms, by generating a heating-impulse response for a transmit-coil, a gradient system, and a magnet for a given set of input waveforms. Furthermore, the interaction extent of an imaging system is evaluated by at least one of measuring and determining a value, corresponding to an equivalent sound pressure level that is created by the sequence over a set period of time.

Still referring back to FIGS. 2A and 2B, in other embodiments, the interaction extent of an imaging system is evaluated by at least one of measuring and determining a value, such as a value corresponding to a magnet temperature dependence relationship, the magnet temperature dependence relationship comprising at least one frequency component of at least one requested gradient waveform. Magnet heating may depend on a frequency component as well as on a raw RMS of a magnetic field as a function of temperature, dB/dt. In other embodiments, the interaction extent of an imaging system is evaluated by at least one of measuring and determining a value, corresponding to at least one of a magnet temperature increase, a transmit-coil temperature increase, a gradient-coil temperature increase in relation to a saved sequence protocol.

Still referring back to FIGS. 2A and 2B, the interaction extent of a patient is evaluated by at least one of measuring and determining a value, corresponding to at least one of a specific absorption rate (SAR) and a transmit-coil heating). Further, the interaction extent of a patient is evaluated by at least one of measuring and determining a value, corresponding to at least one overall patient experience metric for each sequence, wherein determining, e.g., strategically, intelligently ordering, certain imaging sequences, is based on an average patient experience rating over a set time interval, and wherein the average patient experience rating is determined by implementing a series of experiments. Furthermore, the interaction extent of a patient is evaluated by at least one of measuring and determining a value, corresponding to a plurality of overall patient experience metrics for each sequence.

Still referring back to FIGS. 2A and 2B, the system and methods of the present disclosure involve determining an optimal sequence organization comprising: evaluating each, and every, combination and each, and every, permutation of each, and every, parameter relating to each imaging sequence of a plurality of imaging sequences; selecting a plurality of imaging sequences based on a lowest total interaction extent, based on a lowest interaction extent of the imaging system and a lowest interaction extent of the patient; and ordering the plurality of imaging sequences, based on the lowest interaction extent of the imaging system and the lowest interaction extent of the patient, wherein each, and every, parameter, relating to each imaging sequence comprises at least one of an overall imaging system heating, a shortest scanner duration, including any downtime to reduce heating, a maximum acoustic energy over a set time interval, e.g., approximately 5 minutes), and the like.

Still referring back to FIGS. 2A and 2B, the system and methods of the present disclosure involve determining an optimal sequence organization comprising: ordering a plurality imaging sequences from a lowest total interaction extent to a highest total interaction extent, based on a lowest interaction extent of the imaging system and a lowest interaction extent of the patient to a highest interaction extent of the imaging system and a highest interaction extent of the patient; and ordering the plurality of imaging sequences, based on the lowest interaction extent of the imaging system and the lowest interaction extent of the patient, based on the lowest total interaction extent to the highest total interaction extent, whereby imaging information is maximized in the event of any interruption to operation of the imaging system, e.g., from overheating.

Still referring back to FIGS. 2A and 2B, the system and methods of the present disclosure alternatively involve determining an optimal sequence organization comprising: evaluating each, and every, combination and each, and every, permutation of each, and every, parameter relating to each imaging sequence of a plurality of imaging sequences; selecting a first imaging sequence of a plurality of imaging sequences based on a highest total interaction extent comprising a highest interaction extent of the imaging system and a highest interaction extent of the patient; selecting a second imaging sequence of the plurality of imaging sequences based on a lowest total interaction extent comprising a lowest interaction extent of the imaging system and a lowest interaction extent of the patient; selecting a third imaging sequence of the plurality of imaging sequences based on a second highest total interaction extent comprising a second highest interaction extent of the imaging system and a second highest interaction extent of the patient; selecting a fourth imaging sequence of the plurality of imaging sequences based on a second lowest total interaction extent comprising a second lowest interaction extent of the imaging system and a lowest highest interaction extent of the patient; and ordering the plurality of imaging sequences accordingly, wherein each, and every, parameter, relating to each imaging sequence comprises at least one of an overall imaging system heating, a shortest scanner duration, including any downtime to reduce heating, a maximum acoustic energy over a set time interval, e.g., approximately 5 minutes), and the like.

Figure 3A:
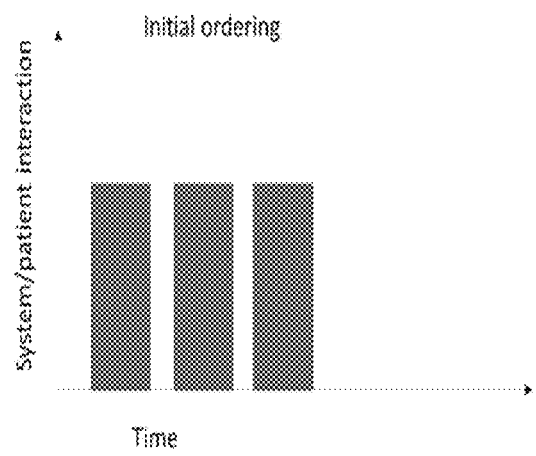
FIG. 3A is a graph illustrating yet another interaction extent of at least one of an imaging system and a patient as a function of time, based on another initial ordering of a plurality of sequences.

Referring to FIG. 3A, this graph illustrates yet another interaction extent of at least one of an imaging system and a patient (ordinate axis) as a function of time (abscissa axis), based on another initial ordering 300A of a plurality of sequences, in accordance with an embodiment of the present disclosure. Each sequence of the plurality of sequences having a corresponding interaction extent value of at least one of an imaging system and a patient (ordinate axis) as a function of time (abscissa axis).

Figure 3B:
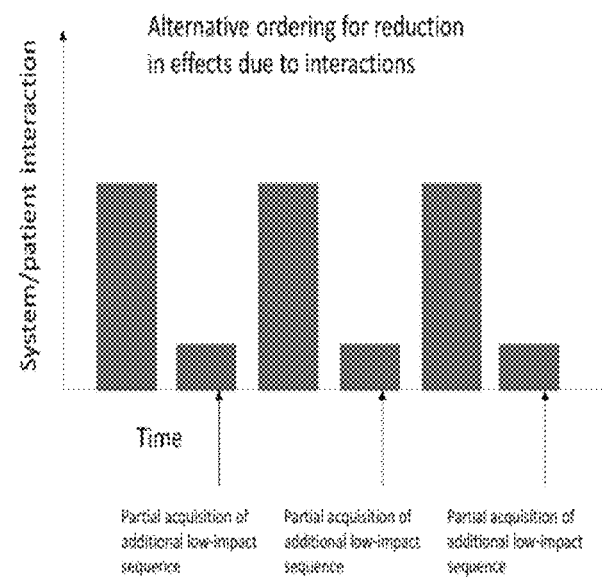
FIG. 3B is a graph illustrating yet another interaction extent of at least one of an imaging system and a patient as a function of time, as shown in FIG. 3A, based on an alternative ordering of the plurality of sequences, wherein the alternative ordering is automatically determined by way of an automatic protocolling system.

Referring to FIG. 3B, this graph illustrates yet another interaction extent of at least one of an imaging system and a patient (ordinate axis) as a function of time (abscissa axis), as shown in FIG. 3A, based on an alternative ordering 300B of the plurality of sequences, wherein the alternative ordering 300B is automatically determined by way of an automatic protocolling system S (FIG. 4), in accordance with an embodiment of the present disclosure. The alternative ordering 300B facilitates an overall reduction in interaction effects.

Still referring to FIG. 3B, to improve an overall patient experience, the automatic protocolling system S automatically determines and instructs placement of a low-intensity sequence, e.g., having a low-intensity acoustic energy, at the end of protocol, thereby mitigating a patient's perception of overall intensity of the imaging experience. If a low-intensity sequence does not exist in the initial order, as shown in FIG. 3A, the automatic protocolling system S automatically determines and instructs placement of a low-intensity sequence, e.g., regardless of whether such low-intensity sequence is configured to acquire data, thereby mitigating a patient's perception of overall intensity of the imaging experience. For example, the alternative ordering 300B comprises a low-intensity sequence which is partially executed.

Figure 4:
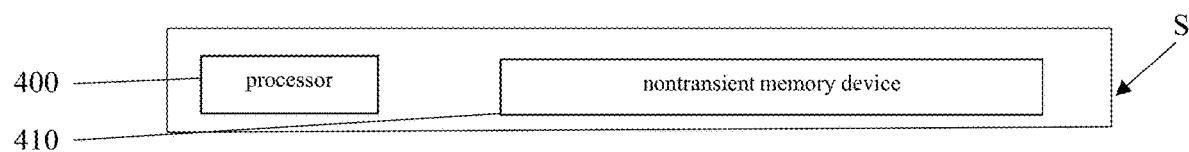
FIG. 4 is a schematic diagram illustrating an automatic protocolling system.

Referring to FIG. 4 and referring back to FIGS. 1A-3B, this schematic diagram illustrates an automatic protocolling system S, in accordance with an embodiment of the present disclosure. The automatic protocolling system S comprises: processor 400 operable by way of a set of executable instructions storable in relation to a nontransient memory device 410, the set of executable instructions configuring the processor to: receive information relating to an initial ordering corresponding to an initial protocol, such as the initial orderings 100A, 200A, 300A, the information comprising data relating to the interaction extent value of at least one of an imaging system and a patient (ordinate axis) as a function of time (abscissa axis) corresponding to each sequence in the plurality of sequences; intelligently determine an alternative ordering, such as the alternative orderings 100B, 200B, 300B by using machine-learning, whereby an alternative protocol is provided; and instructing an imaging system, such as an MRI system (not shown), to operate by using the alternative protocol.

Still referring to FIG. 4, an automatic protocolling system S comprises a processor 400 operable by way of a set of executable instructions storable in relation to a nontransient memory device 410, the set of executable instructions configuring the processor 400 to: receive information relating to an initial protocol comprising an initial ordering of a plurality of sequences, the information comprising data relating to an interaction extent value of at least one of an imaging system and a patient as a function of time corresponding to each sequence in the plurality of sequences, the data relating to a time-integrated effect of each sequence in the plurality of sequences; and dynamically determine an alternative protocol comprising an alternative ordering of the plurality of sequences based on the time-integrated effect, whereby an alternative protocol is provided, in accordance with an embodiment of the present disclosure. Information relating to at least one effect on the imaging system comprises information relating to at least one of: a gradient root-mean-square (RMS) current, an RMS B1+ power, a magnet heating, a magnet drift, an acoustic response, and a transmit-coil heating, a gradient-amplifier heating, an RF-amplifier heating, and shim-amplifier heating.

Still referring to FIG. 4, an automatic protocolling system S comprises a processor 400 operable by way of a set of executable instructions storable in relation to a nontransient memory device 410, the set of executable instructions configuring the processor 400 to: receive information relating to an initial protocol comprising an initial ordering of a plurality of sequences, the information comprising data relating to an interaction extent value of at least one of an imaging system and a patient as a function of time corresponding to each sequence in the plurality of sequences; and dynamically determine an alternative protocol comprising an alternative ordering of the plurality of sequences, whereby an alternative protocol is provided, in accordance with an embodiment of the present disclosure.

Still referring to FIG. 4, in general, the processor 400 of the automatic protocolling system S is configured to intelligently reorder an initial protocol comprising an initial plurality of sequences, such as a set of magnetic resonance (MR) sequences, to at least one of: reduce intra-scanner interactions, reduce scanner to patient interactions, and improve overall patient experience, whereby an alternative protocol comprising a reordered plurality of sequences is provided. In an example implementation, effects of running protocol comprising an initial plurality of sequences can be modelled and predicted in advance by way of the automatic protocolling system S, based on information relating to operation of the imaging system, such as the MRI system, as whole.

Still referring to FIG. 4, for instance, effects on the patient, e.g., specific absorption rate (SAR) "lookahead" and peripheral nerve stimulation (PNS), as well as system component interactions, e.g., prediction of gradient root mean square (RMS) currents, RMS B1+ power, magnet heating/drift, and acoustic responses, are predicted by way of the automatic protocolling system S and used to instruct an imaging system, e.g., an MRI system, to operate by running the alternative protocol comprising the reordered plurality of sequences. The processor 400 of the automatic protocolling system S is further configured to dynamically reorder the plurality of sequences of the initial protocol, e.g., as described in relation to FIGS. 1A-2B, whereby a dynamically reordered protocol is provided, and to automatically instruct the imaging system to run the dynamically reordered protocol top, e.g., in real-time. For example, if a dynamically reordered protocol comprising a reordered plurality of sequences is provided, the processor 400 of the automatic protocolling system S is further configured to dynamically instruct the imaging system to forgo running any previous protocols which has not yet run and to run the dynamically reordered protocol, whereby the overall interaction extent is reduced.

Still referring to FIG. 4, alternatively, the processor 400 of the automatic protocolling system S is further configured to dynamically optimize reordering of the plurality of sequences when configuring scan protocols, wherein the processor 400 is configured to suggest a preferred sequence order to minimize interaction extent. Due to medical need, radiologists, technologists, or other users may prefer acquiring certain sequences in a priority order. The processor 400 of the automatic protocolling system S is further configured to dynamically reorder the plurality of sequences by using information relating to a user-defined priority.

Still referring to FIG. 4, the processor 400 of the automatic protocolling system S is further configured to suggest to the user a set of non-interacting sequences to be run between two highly-interacting sequences of an initial protocol or a previous protocol, rather than performing no action as otherwise would occur in the related art. In one implementation, the processor 400 of the automatic protocolling system S is further configured to automatically place non-interacting sequences between highly-interacting sequences in order to at least one of: update calibration data, acquire partial or full quantitative data, and other data that may be useful for final diagnosis or image processing, by examples only.

Still referring to FIG. 4, the processor 400 of the automatic protocolling system S is further configured to dynamically instruct a display device to dynamically display a representation of at least one metric, viewable by a user, during dynamic configuration of scan protocols, e.g., as a reordered protocol comprising a reordered plurality of sequences is determined. The at least one metric provides quantification of the relative merits between different sequence orderings. For example, the processor 400 of the automatic protocolling system S is further configured to suggest a preferred order for the plurality of sequences to minimize hardware effects; and the at least one metric is used to convey, to the user, information relating to a quantifiable benefit to the imaging system. The user could use this information, relating to the quantifiable benefit, in deciding whether to accept a suggested reordered protocol. Since the user may be ultimately required to choose between competing concerns, e.g. priority order versus hardware effects, providing the information, relating to the quantifiable benefit to the imaging system, is also beneficial for the user in having information relating to the impact of a suggested reordered protocol.

Figure 5:
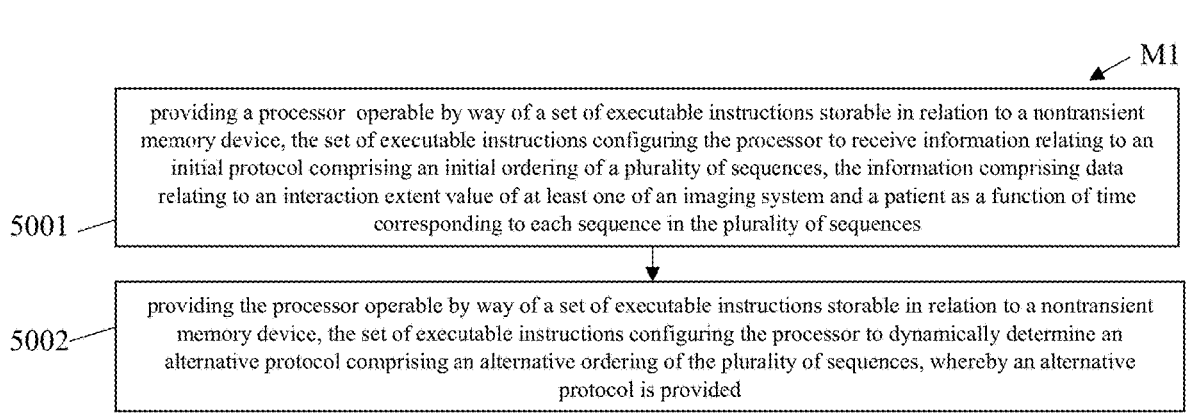
FIG. 5 is a flow diagram illustrating a method of providing an automatic protocolling system.

Referring to FIG. 5, this flow diagram illustrates a method M1 of providing an automatic protocolling system S, in accordance with an embodiment of the present disclosure. The method M1 comprises: providing a processor 400 operable by way of a set of executable instructions storable in relation to a nontransient memory device 410, the set of executable instructions configuring the processor 400 to: receive information relating to an initial protocol comprising an initial ordering of a plurality of sequences, the information comprising data relating to an interaction extent value of at least one of an imaging system and a patient as a function of time corresponding to each sequence in the plurality of sequences, as indicated by block 5001; and dynamically determine an alternative protocol comprising an alternative ordering of the plurality of sequences, whereby an alternative protocol is provided, as indicated by block 5002.

Still referring to FIG. 5, alternatively, the method M1 comprises: providing a processor 400 operable by way of a set of executable instructions storable in relation to a nontransient memory device 410, the set of executable instructions configuring the processor 400 to: receive information relating to a protocol, such as a suggested study protocol; determine an interaction extent of a plurality of sequences in the protocol; and one of dynamically order and dynamically reorder the protocol, whereby an alternative protocol corresponding to a preferred interaction extent is provided. The method M1, alternatively, further comprises providing the processor 400 operable by way of the set of executable instructions storable in relation to a nontransient memory device 410, the set of executable instructions configuring the processor 400 to output the alternative protocol, such as to a controller of the imaging system, an internal device, an external device, e.g., a display device, and the like.

Figure 6:
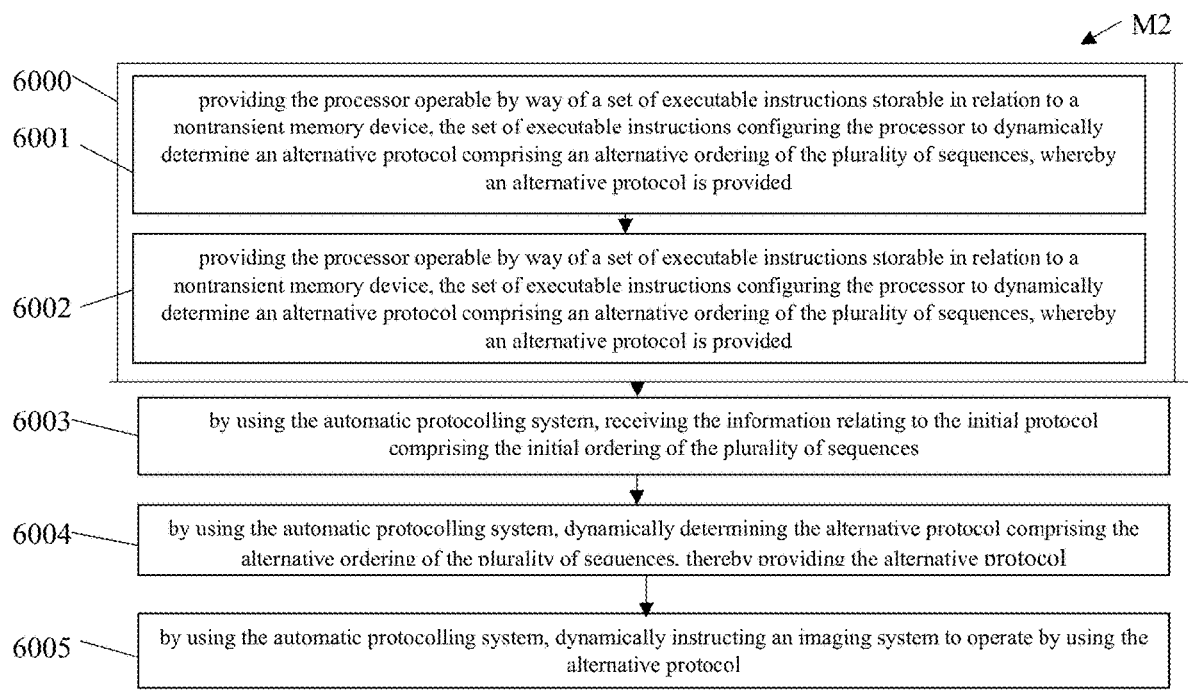
FIG. 6 is a flow diagram illustrating a method of automatic protocolling by way of an automatic protocolling system.

Referring to FIG. 6, this flow diagram illustrates a method M2 of automatically protocolling by way of an automatic protocolling system S, in accordance with an embodiment of the present disclosure. The method M2 comprises: providing the automatic protocolling system S, as indicated by block 6000, providing the automatic protocolling system S, as indicated by block 6000, comprising providing a processor 400 operable by way of a set of executable instructions storable in relation to a nontransient memory device 410, the set of executable instructions configuring the processor 400 to: receive information relating to an initial protocol comprising an initial ordering of a plurality of sequences, the information comprising data relating to an interaction extent value of at least one of an imaging system and a patient as a function of time corresponding to each sequence in the plurality of sequences as indicated by block 6001; and dynamically determine an alternative protocol comprising an alternative ordering of the plurality of sequences, whereby an alternative protocol is provided, as indicated by block 6002; by using the automatic protocolling system, receiving the information relating to the initial protocol comprising the initial ordering of the plurality of sequences, as indicated by block 6003; and dynamically determining the alternative protocol comprising the alternative ordering of the plurality of sequences, thereby providing the alternative protocol, as indicated by block 6004; and dynamically instructing an imaging system to operate by using the alternative protocol, as indicated by block 6005.

Still referring to FIG. 6, alternatively, the method M1 comprises: providing a processor 400 operable by way of a set of executable instructions storable in relation to a nontransient memory device 410, the set of executable instructions configuring the processor 400 to: receive information relating to a protocol, such as a suggested study protocol; determine an interaction extent of a plurality of sequences in the protocol; and one of dynamically order and dynamically reorder the protocol, whereby an adjusted protocol corresponding to a preferred interaction extent is provided. The method M1, alternatively, further comprises providing the processor 400 operable by way of the set of executable instructions storable in relation to a nontransient memory device 410, the set of executable instructions configuring the processor 400 to output the adjusted protocol, such as to a controller of the imaging system, an internal device, an external device, e.g., a display device, and the like.

While the present disclosure describes various embodiments for illustrative purposes, such description is not intended to be limited to such embodiments. On the contrary, the Applicant's teachings described and illustrated herein encompass various alternatives, modifications, and equivalents, without departing from the embodiments, the general scope of which is defined in the appended claims. Except to the extent necessary or inherent in the methods or the processes, themselves, no particular order to steps or stages of the methods or the processes herein described is intended or implied. In many cases, the order of process steps may be varied without changing the purpose, effect, or import of the methods or the processes herein described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments, such as any combination of any feature herein disclosed, which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public, regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

What is claimed is:

1. An automatic protocolling system, comprising a processor operable by way of a set of executable instructions storable in relation to a nontransient memory device, the set of executable instructions configuring the processor to:
   receive information relating to an initial protocol comprising an initial ordering of a plurality of sequences, the information comprising data relating to an interaction extent value of at least one of an imaging system and a patient as a function of time corresponding to each sequence in the plurality of sequences, the data relating to a time-integrated effect of each sequence in the plurality of sequences;
   dynamically determine an alternative protocol comprising an alternative ordering of the plurality of sequences based on the time-integrated effect, whereby an alternative protocol is provided;
   dynamically instruct an imaging system to operate by using the alternative protocol;
   dynamically determine the alternative protocol by using artificial intelligence;
   dynamically determine the alternative protocol based on information relating to operation of the imaging system;
   dynamically determine the alternative protocol by predicting information relating to at least one effect on at least one of the imaging system and a patient;
   forgo running any previous protocol which has not yet run; and run the alternative protocol, whereby overall interaction extent is reduced;
   dynamically optimize reordering of the plurality of sequences when configuring scan protocols; and dynamically suggest a preferred sequence order, whereby overall interaction extent is minimized;
   dynamically reorder the plurality of sequences by using information relating to a user-defined priority;
   dynamically suggest a set of non-interacting sequences to run between two highly-interacting sequences of the initial protocol;
   automatically place at least one non-interacting sequence between two highly-interacting sequences;
   dynamically instruct a display device to dynamically display a representation of at least one metric during dynamic configuration of scan protocols; and
   dynamically suggest a preferred order for the plurality of sequences,
   wherein the artificial intelligence comprises machine-learning,
   wherein the imaging system comprises a magnetic resonance imaging (MRI) system,
   wherein the information relating to at least one effect on the imaging system comprises information relating to at least one of: a gradient root-mean-square (RMS) current, an RMS B1+ power, a magnet heating, a magnet drift, an acoustic response, and a transmit-coil heating, a gradient-amplifier heating, an RF-amplifier heating, and shim-amplifier heating, wherein the information relating to at least one effect on the patient comprises information relating to at least one of: a specific absorption rate (SAR) and a peripheral nerve stimulation (PNS), and wherein the at least one metric provides quantification of the relative merits between different sequence orderings.

2. The automatic protocolling system of claim 1, wherein the set of executable instructions further configure the processor to dynamically instruct an imaging system to operate by using the alternative protocol.

3. The automatic protocolling system of claim 2, wherein the imaging system comprises a magnetic resonance imaging (MRI) system.

4. The automatic protocolling system of claim 1, wherein the set of executable instructions further configure the processor to dynamically determine the alternative protocol by using artificial intelligence.

5. The automatic protocolling system of claim 4, wherein the artificial intelligence comprises machine-learning.

6. The automatic protocolling system of claim 1, wherein the set of executable instructions further configure the processor to dynamically determine the alternative protocol based on information relating to operation of the imaging system.

7. The automatic protocolling system of claim 1, wherein the set of executable instructions further configure the processor to dynamically determine the alternative protocol by predicting information relating to at least one effect on at least one of the imaging system and a patient.

8. The automatic protocolling system of claim 7, wherein the information relating to at least one effect on the imaging system comprises information relating to at least one of: a gradient root-mean-square (RMS) current, an RMS B1+ power, a magnet heating, a magnet drift, an acoustic response, and a transmit-coil heating, a gradient-amplifier heating, an RF-amplifier heating, and shim-amplifier heating.

9. The automatic protocolling system of claim 7, wherein the information relating to at least one effect on the patient comprises information relating to at least one of: a specific absorption rate (SAR) and a peripheral nerve stimulation (PNS).

10. The automatic protocolling system of claim 1, wherein the set of executable instructions further configure the processor to: forgo running any previous protocol which has not yet run; and run the alternative protocol, whereby overall interaction extent is reduced.

11. The automatic protocolling system of claim 1, wherein the set of executable instructions further configure the processor to: dynamically optimize reordering of the plurality of sequences when configuring scan protocols; and dynamically suggest a preferred sequence order, whereby overall interaction extent is minimized.

12. The automatic protocolling system of claim 1, wherein the set of executable instructions further configure the processor to: dynamically reorder the plurality of sequences by using information relating to a user-defined priority.

13. The automatic protocolling system of claim 1, wherein the set of executable instructions further configure the processor to: dynamically suggest a set of non-interacting sequences to run between two highly-interacting sequences of the initial protocol.

14. The automatic protocolling system of claim 1, wherein the set of executable instructions further configure the processor to: automatically place at least one non-interacting sequence between two highly-interacting sequences.

15. The automatic protocolling system of claim 1, wherein the set of executable instructions further configure the processor to: dynamically instruct a display device to dynamically display a representation of at least one metric during dynamic configuration of scan protocols.

16. The automatic protocolling system of claim 15, wherein the at least one metric provides quantification of the relative merits between different sequence orderings.

17. The automatic protocolling system of claim 1, wherein the set of executable instructions further configure the processor to: suggest a preferred order for the plurality of sequences.

18. A method of providing an automatic protocolling system, the method comprising providing a processor operable by way of a set of executable instructions storable in relation to a nontransient memory device, the set of executable instructions configuring the processor to:

receive information relating to an initial protocol comprising an initial ordering of a plurality of sequences, the information comprising data relating to an interaction extent value of at least one of an imaging system and a patient as a function of time corresponding to each sequence in the plurality of sequences, the data relating to a time-integrated effect of each sequence in the plurality of sequences;

dynamically determine an alternative protocol comprising an alternative ordering of the plurality of sequences based on the time-integrated effect, whereby an alternative protocol is provided;

dynamically instruct an imaging system to operate by using the alternative protocol;

dynamically determine the alternative protocol by using artificial intelligence;

dynamically determine the alternative protocol based on information relating to operation of the imaging system;

dynamically determine the alternative protocol by predicting information relating to at least one effect on at least one of the imaging system and a patient;

forgo running any previous protocol which has not yet run; and run the alternative protocol, whereby overall interaction extent is reduced;

dynamically optimize reordering of the plurality of sequences when configuring scan protocols; and dynamically suggest a preferred sequence order, whereby overall interaction extent is minimized;

dynamically reorder the plurality of sequences by using information relating to a user-defined priority;

dynamically suggest a set of non-interacting sequences to run between two highly-interacting sequences of the initial protocol;

automatically place at least one non-interacting sequence between two highly-interacting sequences;

dynamically instruct a display device to dynamically display a representation of at least one metric during dynamic configuration of scan protocols; and dynamically suggest a preferred order for the plurality of sequences, wherein the artificial intelligence comprises machine-learning, wherein the imaging system comprises a magnetic resonance imaging (MRI) system, wherein the information relating to at least one effect on the imaging system comprises information relating to at least one of: a gradient root-mean-square (RMS) current, an RMS B1+ power, a magnet heating, a magnet drift, an acoustic response, and a transmit-coil heating, a gradient-amplifier heating, an RF-amplifier heating, and shim-amplifier heating, wherein the information relating to at least one effect on the patient comprises information relating to at least one of: a specific absorption rate (SAR) and a peripheral nerve stimulation (PNS), and wherein the at least one metric provides quantification of the relative merits between different sequence orderings.

19. A method of automatically protocolling by way of an automatic protocolling system, the method comprising:

providing the automatic protocolling system, providing the automatic protocolling system comprising providing a processor operable by way of a set of executable instructions storable in relation to a nontransient memory device, the set of executable instructions configuring the processor to: receive information relating to an initial protocol comprising an initial ordering of a plurality of sequences, the information comprising data relating to an interaction extent value of at least one of an imaging system and a patient as a function of time corresponding to each sequence in the plurality of sequences, the data relating to a time-integrated effect of each sequence in the plurality of sequences; and dynamically determine an alternative protocol comprising an alternative ordering of the plurality of sequences based on the time-integrated effect, whereby an alternative protocol is provided;

by using the automatic protocolling system, receiving the information relating to the initial protocol comprising the initial ordering of the plurality of sequences;

dynamically determining the alternative protocol comprising the alternative ordering of the plurality of sequences, thereby providing the alternative protocol;

dynamically instructing an imaging system to operate by using the alternative protocol;

dynamically instruct an imaging system to operate by using the alternative protocol;

dynamically determine the alternative protocol by using artificial intelligence;

dynamically determine the alternative protocol based on information relating to operation of the imaging system;

dynamically determine the alternative protocol by predicting information relating to at least one effect on at least one of the imaging system and a patient;

forgo running any previous protocol which has not yet run; and run the alternative protocol, whereby overall interaction extent is reduced;

dynamically optimize reordering of the plurality of sequences when configuring scan protocols; and dynamically suggest a preferred sequence order, whereby overall interaction extent is minimized;

dynamically reorder the plurality of sequences by using information relating to a user-defined priority;

dynamically suggest a set of non-interacting sequences to run between two highly-interacting sequences of the initial protocol;

automatically place at least one non-interacting sequence between two highly-interacting sequences;

dynamically instruct a display device to dynamically display a representation of at least one metric during dynamic configuration of scan protocols; and dynamically suggest a preferred order for the plurality of sequences, wherein the artificial intelligence comprises machine-learning, wherein the imaging system comprises a magnetic resonance imaging (MRI) system, wherein the information relating to at least one effect on the imaging system comprises information relating to at least one of: a gradient root-mean-square (RMS) current, an RMS B1+ power, a magnet heating, a magnet drift, an acoustic response, and a transmit-coil heating, a gradient-amplifier heating, an RF-amplifier heating, and shim-amplifier heating, wherein the information relating to at least one effect on the patient comprises information relating to at least one of: a specific absorption rate (SAR) and a peripheral nerve stimulation (PNS), and wherein the at least one metric provides quantification of the relative merits between different sequence orderings.

* * * * *